United States Patent
Yang et al.

(10) Patent No.: US 10,045,718 B2
(45) Date of Patent: Aug. 14, 2018

(54) METHOD AND APPARATUS FOR USER-TRANSPARENT SYSTEM CONTROL USING BIO-INPUT

(71) Applicant: Atheer, Inc., Mountain View, CA (US)

(72) Inventors: Allen Yang Yang, Richmond, CA (US); Mohamed Nabil Hajj Chehade, Los Angeles, CA (US); Sina Fateh, Mountain View, CA (US); Sleiman Itani, East Palo Alto, CA (US)

(73) Assignee: Atheer, Inc., Mountain View, CA (US)

( * ) Notice: Subject to any disclaimer, the term of this patent is extended or adjusted under 35 U.S.C. 154(b) by 9 days.

(21) Appl. No.: 14/087,452

(22) Filed: Nov. 22, 2013

(65) Prior Publication Data

US 2014/0159862 A1 Jun. 12, 2014

Related U.S. Application Data

(60) Provisional application No. 61/729,412, filed on Nov. 22, 2012.

(51) Int. Cl.
| | |
|---|---|
| *G06F 1/16* | (2006.01) |
| *A61B 5/1171* | (2016.01) |
| *A61B 5/117* | (2016.01) |
| *G07C 9/00* | (2006.01) |
| *G06F 21/10* | (2013.01) |

(Continued)

(52) U.S. Cl.
CPC ............ *A61B 5/1171* (2016.02); *A61B 5/117* (2013.01); *A61B 5/6803* (2013.01); *G06F 1/163* (2013.01); *G06F 3/015* (2013.01); *G06F 21/10* (2013.01); *G06K 9/00885* (2013.01); *G07C 9/00158* (2013.01); *A61B 5/7445* (2013.01); *G06K 2009/00939* (2013.01)

(58) Field of Classification Search
CPC ................ G07C 9/00158; G06F 1/163; G06K 2009/00939
USPC ........................................................ 340/5.52
See application file for complete search history.

(56) References Cited

U.S. PATENT DOCUMENTS

| | | | | |
|---|---|---|---|---|
| 5,626,145 A | * | 5/1997 | Clapp ................ | A61B 5/04008 600/544 |
| 5,844,824 A | * | 12/1998 | Newman ................ | G06F 3/011 345/156 |

(Continued)

*Primary Examiner* — Vernal Brown
(74) *Attorney, Agent, or Firm* — Mohr Intellectual Property Law Solutions, P.C.

(57) ABSTRACT

A wearable sensor vehicle with a bio-input sensor and a processor. When the vehicle is worn, the sensor is arranged so as to sense bio-input from the user. The sensor senses bio-input, the processor compares the bio-input to a standard, and if the standard is met the processor indicates a response. The user may be uniquely identified from the bio-input. One or more systems on or communicating with the vehicle may be controlled transparently, without requiring direct action by the user. Control actions may include security identification of the user, logging in to accounts or programs, setting preferences, etc. The sensor collects bio-input substantially without instruction or dedicated action from the user; the processor compares bio-input against the standard substantially without instruction or dedicated action from the user; and the processor generates and/or implements a response based on the bio-input substantially without instruction or dedicated action from the user.

45 Claims, 7 Drawing Sheets

(51) Int. Cl.
  *G06F 3/01*  (2006.01)
  *G06K 9/00*  (2006.01)
  *A61B 5/00*  (2006.01)

(56) References Cited

U.S. PATENT DOCUMENTS

| | | | |
|---|---|---|---|
| 6,993,378 B2* | 1/2006 | Wiederhold | A61B 5/02055 |
| | | | 382/115 |
| 7,796,013 B2* | 9/2010 | Murakami | G06F 21/32 |
| | | | 340/5.52 |
| 8,773,239 B2* | 7/2014 | Phillips | A61B 5/117 |
| | | | 340/5.82 |
| 2007/0049844 A1* | 3/2007 | Rosenfeld | A61B 5/04842 |
| | | | 600/544 |
| 2008/0216171 A1* | 9/2008 | Sano | H04L 9/32 |
| | | | 726/19 |
| 2013/0096453 A1* | 4/2013 | Chung | G06F 3/04847 |
| | | | 600/544 |

* cited by examiner

METHOD AND APPARATUS FOR USER-TRANSPARENT SYSTEM CONTROL USING BIO-INPUT

PRIORITY CLAIM

This application claims the benefit of U.S. Provisional Application Ser. No. 61/729,412 filed on Nov. 22, 2012, the contents of which are incorporated by reference for all intents and purposes.

FIELD OF THE INVENTION

This invention relates to biometric control systems. More particularly, this invention relates to systems for initiating actions based on biometric parameters, substantially without requiring positive instruction from a user of those systems.

DESCRIPTION OF RELATED ART

Sensing and monitoring biological parameters can be used to monitor health, provide user feedback, identify individuals, and/or confirm their identity. The latter two approaches sometimes are referred to as biometrics, that is, identification based on individuals' characteristic biology. Signals used in biometric evaluation Biometric evaluation may have advantages, for example in that counterfeiting biological traits can be extremely difficult. Thus, validating an individual based on biometric parameters may provide a high level of confidence that an individual is in fact who he or she claims to be, is authorized to use some device or access information, etc.

However, conventional biometric systems may be cumbersome, and/or limited in their usability. Conventional biometric may comparisons require active instruction and control from a user, including but not limited to wearing and/or positioning sensors specifically for the purposes of biometrics. For example, a system based on fingerprint identification might require a user to place one or more fingers on a scanning pad, and hold them there while the system reads and evaluated the user's prints, a system that uses retinal recognition might require a user to look into a camera for some period with an eye fixed and open, etc. No clear advantage may be apparent to the user to offset the time and trouble, which may detract from usability.

In addition, requiring a user to actively operate a biometric sensing system also requires that the user familiarize himself or herself with that system to a sufficient degree as to know what actions he or she must take. For example, for a user using a retinal scan system for the first time it may not be obvious how close to position the eye relative to the sensor, how long to remain motionless, where to look during the evaluation, etc. As the number of biometric parameters that could be sensed is large, and the variety of specific procedures that can be used to implement sensing is likewise large, this can be problematic.

Furthermore, biometric activation typically is a one-time event. That is, a user may validate their identity only at the beginning of a session using (for example) a secure computing system. Should the validated user leave without logging out, it may be possible for an unauthorized user to take over use of the system without having to be validated. While it is technically possible to require periodic re-validation, this added security increases the burden on the user, and so makes the system less useful.

BRIEF SUMMARY OF THE INVENTION

The present invention contemplates a variety of systems, apparatus, methods, and paradigms for user-transparent system control using bio-input.

In one embodiment of the present invention, an apparatus is provided that includes a vehicle adapted to be worn by a subject. At least one sensor is disposed on the vehicle, the sensor being adapted to sense at least one bio-input of the subject. The apparatus includes a processor in communication with the sensor. The vehicle and sensor are configured such that when the subject wears the vehicle, the sensor is substantially disposed with respect to the subject for sensing the bio-input. The sensor is adapted to sense the bio-input with substantially no dedicated sensing action required from the subject. The processor is adapted to compare the bio-input with a standard therefor, and to indicate a response if the bio-input meets the standard.

The vehicle may be a head-mounted display. The sensor may be adapted to sense a cardiac wave of the subject, a brain wave of the subject, a retinal pattern of the subject, an iris pattern of the subject, a vein pattern of the subject, a skin texture pattern of the subject, a facial color distribution of the subject, and/or a facial shape of the subject.

The sensor may be an electrocardiogram, a magnetocardiogram, an electroencephalogram, a magnetoencephalogram, a monochromatic visible light imager, a color visible light imager, a monochromatic near-infrared imager, a color near-infrared imager, a spectrometer, an imaging spectrometer, a time-of-flight sensor, and/or a structured light sensor.

The sensor may be a contact sensor. The sensor may be a non-contact sensor.

The sensor may be disposed on the vehicle such that when the subject wears the vehicle, the sensor is proximate a bridge of a nose of the subject. The sensor may be disposed on the vehicle such that when the subject wears the vehicle, the sensor is proximate a temple of the subject. The sensor may be disposed on the vehicle such that when the subject wears the vehicle, the sensor is behind and proximate an ear of the subject. The sensor may be disposed on the vehicle such that when the subject wears the vehicle, the sensor is proximate a forehead of the subject.

The sensor may be removably engaged with the vehicle.

The response may include activating an entity, authorizing access to the entity, and/or activating preferences in the entity.

The entity may include at least one of an electronic device, an electronic device component, and a data entity including executable instructions.

The apparatus may include a communicator adapted to communicate between the processor and an external entity.

The response may include establishing communication between the processor and the external entity. The response may include communicating the bio-input, the time of sensing the bio-input, and/or the location of sensing the bio-input.

The processor may be adapted to record data. The processor may be adapted to record the bio-input, the time of sensing the bio-input, and/or the location of sensing the bio-input.

The sensor may be adapted to repeatedly sense the bio-input. The processor may be adapted to repeatedly compare the bio-input with the standard therefor. The processor may be adapted to repeatedly indicate the response. The sensor may be adapted to substantially continuously sense the bio-input. The processor may be adapted to substantially continuously compare the bio-input with the standard therefor. The processor may be adapted to substantially continuously indicate the response.

The vehicle may be adapted to perform at least one subject service other than as the vehicle for the sensor.

In another embodiment of the present invention, a method is provided that includes disposing at least one sensor so as to enable sensing at least one bio-input from a subject, the sensor being adapted to sense the bio-input. The method includes sensing with the sensor the bio-input from the subject, the sensing requiring substantially no dedicated sensing action from the subject, comparing the bio-input with at least one standard therefor, and indicating a response if the bio-input meets the standard.

Disposing the sensor in relation to the subject may include disposing the sensor on a vehicle adapted to be worn by the subject.

The method may include sensing a cardiac wave of the subject, a brain wave of the subject, a retinal pattern of the subject, an iris pattern of the subject, a vein pattern of the subject, a skin texture pattern of the subject, a facial color distribution of the subject, and/or a facial shape of the subject. The method may include sensing the bio-input using electrocardiography, magnetocardiography, an electroencephalography, a magnetoencephalography, monochromatic visible light imaging, color visible light imaging, monochromatic near-infrared imaging, color near-infrared imaging, spectrometry, imaging spectrometry, time-of-flight depth sensing, and/or structured light depth sensing.

The method may include sensing the bio-input via contact sensing. The method may include sensing the bio-input via non-contact sensing.

The method may include disposing the sensor proximate a bridge of a nose of the subject. The method may include disposing the sensor behind and proximate an ear of the subject. The method may include disposing the sensor proximate a forehead of the subject.

The method may include removably disposing the sensor on the vehicle adapted to be worn by the subject.

The response may include activating an entity, authorizing access to the entity, and/or activating preferences in the entity.

The entity may include an electronic device, an electronic device component, and/or a data entity including executable instructions.

The response may include performing an action an augmented reality environment and/or a virtual reality environment. The response may include establishing communication between the processor and the external entity. The response may include communicating the bio-input, a time of sensing the bio-input, and/or a location of sensing the bio-input.

The method may include recording the bio-input, the time of sensing the bio-input, and/or the location of sensing the bio-input.

The method may include repeatedly sensing with the sensor the bio-input, repeatedly comparing the bio-input with the standard, and if the bio-input meets the standard, repeatedly executing the response. The method may include substantially continuously sensing with the sensor the bio-input, substantially continuously comparing the bio-input with the standard, and if the bio-input meets the standard, substantially continuously executing the response.

The vehicle may be adapted to perform at least one subject service other than as the vehicle for the sensor. The method may include the vehicle performing at least one subject service other than as the vehicle for the sensor.

In another embodiment of the present invention, an apparatus is provided that includes a vehicle adapted to be worn by a subject, the vehicle including a head-mounted display, the vehicle being adapted to perform at least one subject service other than as the vehicle for the sensor. At least one sensor is disposed on the vehicle such that when the subject wears the vehicle, the sensor is proximate a bridge of a nose of the subject, the sensor being a color visible light imaging sensor adapted to sense a cardiac wave of the subject. The apparatus also includes a processor in communication with the sensor. The vehicle and the sensor are configured such that when the subject wears the vehicle, the sensor is substantially disposed with respect to the subject for sensing the bio-input. The sensor is adapted to repeatedly sense the bio-input with substantially no dedicated sensing action required from the subject. The processor is adapted to repeatedly compare the bio-input with a standard therefor. The processor is adapted to repeatedly indicate a response if the bio-input meets the standard, the response including activating an entity, authorizing access to the entity, and/or activating preferences in the entity, the entity including an electronic device, an electronic device component, and/or a data entity including executable instructions. The processor is adapted to repeatedly record the bio-input, the time of sensing the bio-input, and/or the location of sensing the bio-input.

In another embodiment of the present invention, a method is provided that includes disposing at least one sensor on a vehicle that includes a head-mounted display adapted to be worn by a subject, such that the sensor is enabled to sense at least one bio-input from the subject proximate a bridge of a nose of the subject, the vehicle being adapted to perform at least one subject service other than as the vehicle for the sensor, the sensor also being adapted to sense the bio-input via color visible light imaging, the bio-input including a cardiac wave. The method includes repeatedly sensing with the sensor the bio-input from the subject, the sensing requiring substantially no dedicated sensing action from the subject, repeatedly comparing the bio-input with at least one standard therefor, and repeatedly executing a response if the bio-input meets the standard, the response including activating an entity, authorizing access to the entity, and/or activating preferences in the entity, the entity including an electronic device, an electronic device component, and/or a data entity including executable instructions. The method further includes repeatedly recording the bio-input, the time of sensing the bio-input, and/or the location of sensing the bio-input.

In another embodiment of the present invention, an apparatus is provided that includes means for disposing at least one sensor so as to enable sensing at least one bio-input from a subject, the sensor being adapted to sense the bio-input, means for sensing with the sensor the bio-input from the subject, the sensing requiring substantially no dedicated sensing action from the subject, means for comparing the bio-input with at least one standard therefor, and means for indicating a response if the bio-input meets the standard.

BRIEF DESCRIPTION OF THE SEVERAL VIEWS OF THE DRAWINGS

Like reference numbers generally indicate corresponding elements in the figures.

DETAILED DESCRIPTION OF THE INVENTION

Figure 1:
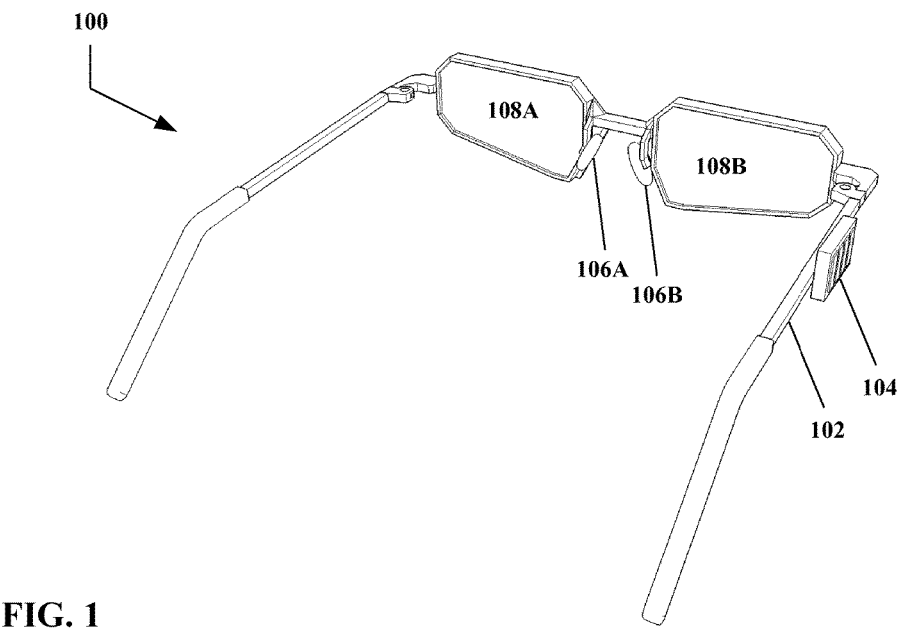
FIG. 1 is a perspective illustration of an example embodiment of an apparatus for user-transparent system control using bio-input according to the present invention, in the form of a head mounted display, with sensor pads proximate the bridge of the nose.

Referring to FIG. 1, therein is shown an example apparatus 100 for user-transparent system control using bio-input according to the present invention.

The example embodiment shown in FIG. 1 includes a vehicle 102 adapted to be worn by a subject or user. The vehicle 102 is a construct that is adapted to support a processor and/or sensors (as described below), and/or other elements of the present invention. However, the vehicle 102 is not particularly limited in form or structure. As shown in FIG. 1, the vehicle 102 takes the form of a pair of glasses or a head mounted display, but this is an example only. Typically though not necessarily the vehicle 102 will take the form of a wearable garment or device with functionality that is useful to the user with or without the bio-input features described herein. For example, head mounted displays (as illustrated), smart watches, and other wearable electronic devices may be suitable vehicles 102. However, these are examples only, and other vehicles 102 may be equally suitable.

The apparatus 100 includes at least one sensor 106A, 106B disposed on the vehicle 102. The sensor 106A, 106B is adapted to sense one or more bio-inputs of a subject.

The present invention is not particularly limited with regard to the type, number, position, and/or arrangement of sensors 106A. 106B (and additional examples of sensors will be presented subsequently herein). The number of potential bio-inputs that could be sensed is extremely broad, and the sensor 106A, 106B is not particularly limited with regard to what parameter(s) the sensor 106A, 106B senses or how that parameter is sensed. For example, an electrocardiographic sensor (sometimes abbreviated ECG or EKG) might be used to identify a characteristic pattern in a user's heartbeat or peripheral pulse, e.g. so as to enable distinguishing one user from another. As shown in FIG. 1, two sensors are present 106A and 106B, in the form of contact pads disposed so as to engage a subject at or proximate the bridge of the subject's nose. Such sensors 106A and 106B may be taken to represent electrical sensors, for example for electrocardiography. However, the arrangement in FIG. 1 is an example only, and other sensors and other parameters may be equally suitable. For example, a magnetocardiographic sensor might be used for similar purposes. Likewise, imagers sensing visible light, infrared light, etc. might be used to measure pulse by examining color, motion, etc. of or in the skin associated with the subject's heartbeat. Alternately, an electroencephalographic or magnetoencephalographic sensor might be used to identify a user's characteristic brainwave patterns. However, these are examples only; other parameters and sensors may be equally suitable, and the present invention is not limited only to the parameters and/or sensors specifically referred to herein.

Sensors 106 may be a contact sensors, operating to sense bio-input via direct or indirect contact with the skin or other outer tissues of the user. However, sensors 106 may also be non-contact sensors, operating to sense bio-input without such contact.

In addition, the position and/or configuration of the sensor(s) 106 may vary considerably from one embodiment to another. The position and/or configuration of sensors 106 will to at least some degree depend on the nature of the bio-input to be sensed, and/or the nature of the particular sensor vehicle 102 for a given embodiment, but the sensor 106 is not otherwise limited.

For example, given an embodiment wherein the sensor vehicle 102 is a headset, and wherein the bio-input is a user's electrocardiogram, sensors 106 might be arranged on or near the headset's nose supports (if any) as shown in FIG. 1, so as to be brought into contact with the user's skin proximate the bridge of the user's nose when the headset is worn. Alternately, however, sensors 106 might be positioned so as to be proximate one or both of the user's temples, to be behind and proximate one or both of the user's ears, or against the user's forehead when the headset is worn. However, these are examples only, and other arrangements may be equally suitable.

Other examples of sensors and positions therefor are shown and described subsequently herein, for example in FIG. 2 through FIG. 8.

For some embodiments, sensors may be removably engaged with the sensor vehicle. In addition, sensors may be a modular units, such as self-contained electrical contact pads, imagers, etc. Removability and/or modularity may facilitate removal and replacement of damaged or nonfunctional sensors, and/or may enable the convenient selection and/or placement of sensors so as to use sensors selected as most suitable for a particular task. For example, sensors might be selected, installed, removed, moved, etc. by a user or other person based on the specific functions that are desired from a given embodiment. One configuration of an apparatus in the form of a head mounted display might utilize contact pads near the bridge of the nose for pulse sensing, but a microphone might be added (with or without removing the contact pads) if voice input is desired, replacement contact pads might be used if the originals are damaged or worn, newer versions of contact sensors might be installed to replace older sensors so as to provide greater functionality, etc. However, such uses of removability and modularity are examples only, and other arrangements may be equally suitable.

It is also noted that sensors need not be adapted to sense a bio-input that is personally identifiable. That is, the bio-input being sensed need not be sufficiently unique as to allow an individual to be reliably identified based on that parameter. Although the use of uniquely identifiable parameters may be useful for some embodiments, e.g. for arrangements wherein the present invention controls security or/and user validation, not all applications require unique identification, and thus not all embodiments require sensing personally identifiable parameters. For example, for some embodiments oxygen saturation, blood pressure, body temperature, etc. might be sensed. These are examples only, and other bio-input may be equally suitable.

Still with reference to FIG. 1, and referring again to the vehicle 102 and the sensors 106, the vehicle 102 may, but is not required to, perform other functions and/or services than supporting the sensors 106 according to the present invention, disposing the sensors 106 with respect to a subject according to the present invention, and/or the sensing of bio-input by the sensors 106 according to the present invention. That is, the vehicle 102 may serve functions not directly related to transparent system control using bio-input.

For example, in the example apparatus 100 illustrated in FIG. 1, the vehicle 102 shown therein is configured as a head mounted display. Although a head mounted display may utilize and/or incorporate transparent system control using bio-input according to the present invention, in general a head mounted display is not necessarily limited only to transparent system control using bio-input according to the present invention. For example, a head mounted display may perform and/or support communication functions, augmented reality functions, virtual reality functions, etc. As a more concrete example, a head mounted display might serve as a tool for displaying videogames, for providing heads-up information to someone driving a vehicle or operating machinery, for delivering street navigation information, etc. Thus, for a head mounted display as described (and potentially including the arrangement shown in FIG. 1, depending on the details of a particular embodiment), the vehicle 102 therefor may perform services for a subject other than being the vehicle for a sensor according to the present invention, and/or other than transparent system control using bio-input according to the present invention.

The apparatus 100 also includes a processor 104 in communication with the sensors 106A, 106B. The processor 104 is adapted to process the bio-input as sensed by the sensors 106A, 106B and communicated from the sensor to the processor. The processor 104 is also adapted to indicate a response if the bio-input meets a standard therefor. In indicating a response, the processor 104 may (but is not required to) execute the response, transmit the response, and/or control some other element in executing the response, for example sending a signal to execute a response (indeed, for at least some embodiments sending the signal may itself be a response, e.g. if the response is to send data), etc. The processor 104 may (but is not required to) generate the response, or may read the response from some data store, utilize a pre-programmed response instantiated on the processor 104, etc.

The present invention is not particularly limited with regard to the choice of processor 104. A range of general-purpose, special-purpose, and embedded systems may be suitable for use as the processor 104. Suitable processors 104 include but are not limited to digital electronic microprocessors. Although the processor 104 is referred to in at least some places herein as a self-contained physical device for purposes of clarity, this is not required, and other arrangements may be suitable. For example, the processor 104 may constitute two or more physical processors working cooperatively, a processing capability in a network without a well-defined physical form, etc.

The processor 104 may be adapted to indicate and/or execute a wide range of responses. For example, in some embodiments the processor 104 might activate some entity, such as an electronic device (or send a signal that the entity should be activated). As a more specific example, the processor 104 might generate a signal that turns on an electronic head-mounted display system, in response to the sensor 106A, 106B sensing the bio-input. Such a response may be conditional; the processor 104 might only generate such an action signal if the bio-input matches a standard therefor, such as the bio-input being within certain ranges, if the bio-input is sensed during certain times of day, etc.

Other responses may include authorizing access to an entity. For example, as noted above the response (and/or the standard applied to the bio-input for determining whether the response is indicated) may be conditional. Thus, for some embodiments the processor 104 might only indicate a response if particular uniquely identifiable bio-input were measured and determined to represent a valid user. The response could authorize access to some entity (e.g. an electronic device) for a valid user with valid bio-input, and deny access for other (invalid) users.

Responses indicated by the processor 104 are not limited only to security purposes. Responses may, for example, provide functionality directly beneficial to a user being sensed by the sensor. For certain embodiments, a response might set preferences for some entity (such as a computer system) based on the identity of the user. Thus, with a particular user having been identified via biometrics, the system can tailor itself to the needs and desires of that user. As a more particular example, stored or imported user preferences such as menu organization, frequently used programs, choice of interface, etc. could be set for a particular after that user is identified through his or her bio-input.

Furthermore, bio-input itself may be useful in personalization for a user. For example, eye position relative to a device such as a head mounted display may vary based on the unique anatomy of a particular user. Thus, the precise location of a user's eyes in relation to the physical structure of (for example) a head mounted display may vary depending on the size of the user's head, the style of the user's hair (e.g. if the head-mounted display is supported partly or entirely on top of the user's head), etc. At least certain such features may vary between uses of a device (e.g. hairstyle), so sensing current bio-input for such features therefor may have advantages over utilizing stored or imported data obtained at some earlier time. For at least some embodiments such personal features could for example affect the position of a user's eyes in relation to image-sensors, cameras, etc. which in turn may affect the appearance of data displayed on screens, the detection of eye motion, etc. Regardless of whether such bio-information as eye position is sufficient for uniquely identifying a user, the measurement of eye position and/or other data may impact certain device function, user experience, etc. Thus for at least certain embodiments, sensing eye position and/or other bio-inputs may enable personalization for improved functionality.

A response might also include establishing a communication link between the processor and some other entity (e.g. a wifi router) based on bio-input sensed by the sensor 106A, 106B. Some embodiments of the present invention may include a communicator in communication with the processor 104 to support the use of such action signals.

In addition, it is noted that responses are not limited to physical events. For some embodiments, responses may sense, alter, control, and/or perform some other action relating to some or all of an augmented reality and/or virtual reality environment. Likewise, responses may include communicating data, including but not limited data regarding and/or related to bio-input. Though such actions might be argued to be insubstantial within the physical world—for example relating entirely to virtual objects, data therefor, etc.—such actions nevertheless may be utilized as part or all of a response according to the present invention.

The aforementioned responses are examples only, and other action signals may be equally suitable.

Again with reference to a processor 104 as shown in FIG. 1, a processor 104 may also be adapted to perform additional functions. For example, a processor 104 may be adapted to record data, either within the processor 104 itself or in some separate data store such as a hard drive, solid state drive, cloud storage system, etc. Data that might be so stored by the processor 104 may include but is not limited to bio-input and/or analytics thereof, the time at which the bio-input was sensed, the location at which the bio-input was sensed, the identity of the subject from whom the bio-input was sensed (for example if the subject is identified from that bio-input), the identity of the processor 104 and/or the apparatus 100 (e.g. using a serial number or other identifier stored within the processor), etc.

In addition, the apparatus 100 may include other elements not necessarily related to functionality regarding transparent system control using bio-control according to the present invention. For example, as shown in FIG. 1 the vehicle 102 takes the form of a head-mounted display, and includes left and right displays 108A and 108B. While such displays 108A and 108B are not necessarily required for the present invention, the present invention also does not exclude such additional elements, or other elements not specifically indicated herein.

Depending on the particulars of a given embodiment, additional element such as displays 108A and 108B may be considered as part of the vehicle 102. Although shown herein for purposes of clarity in describing a specific embodiment having a form of a head mounted display, such elements, structures, etc. may in at least some instances be subsumed within the concept of a vehicle 102 according to the present invention. Thus, the term "vehicle" may extend to include visual displays, audio outputs, wired and/or wireless communications devices, haptic feedback units, optical filters (e.g. polarizing, UV-blocking, and/or colored filters), cosmetic ornamentation, etc. that are not necessarily directly associated with transparent system control using bio-input according to the present invention. Such additional features and elements, while not required, also are not excluded.

As previously noted, the present invention may enable user-transparent system control. That is, control of at least certain portions and/or features of a system may be effected by and/or in response to a user, but with no or substantially no active intervention on the part of the user. Stated somewhat more crudely, the present invention may enable the user to control a system in some fashion, without the user having to actively "do anything".

As an example, consider an arrangement wherein a user's pulse is sensed as bio-input, and wherein the user's pulsed is sensed with sufficient sensitivity as to enable unique identification of a user by his or her characteristic heart function. Consider further that such an arrangement might utilize a vehicle in the form of a head mounted display, perhaps resembling a pair of glasses, with sensors disposed thereon in pads near the bridge of the nose. In such instance, a user may issue commands to the system—i.e. the user may control at least certain features thereof—merely by wearing the vehicle. For example, in putting on the vehicle, the sensors may sense the user's pulse, the processor may establish the user's identity from his or her pulse, and the processor may then turn on display screens or other components, authorize use of the device at some level of operating privileges, log the user in to one or more accounts, set display or interface preferences to values specific to that user, etc.

Such control actions may be executed in the case of the present invention with no or substantially no dedicated action on the part of the user. To continue the example of the head mounted display, the user may not be required to "do anything" to log in, set preferences, turn on the device, etc., besides simply putting on the head mounted display. The user may not even be aware that in putting on the device, he or she is logging in, setting preferences, etc. Thus, although the device is responding to the user and carrying out commands in response thereto, the user is controlling the device in a transparent fashion, without dedicated effort to control the device (and potentially without even being conscious of such control).

Described alternatively, although the present invention may be adapted to sense bio-input from the subject, no or substantially no dedicated action is required by the user to cause or support the sensing. (Although "putting on the head mounted display" might be argued to be considered a user action, the user action in question for such an example would be, in practice, putting on the display. The user is not required to take any specific or additional positive action to active and/or control the sensors, etc.) Likewise, although the present invention may be adapted to compare the bio-input from the subject with a standard therefor, no or substantially no dedicated action is required by the user to cause or support the comparison. Further, although the present invention may be adapted to indicate and/or carry out a response if the bio-input from the subject meets the standard therefor, no or substantially no dedicated action is required by the user to cause or support indicating or carrying out the response.

It is emphasized that the present invention does not prohibit user action for sensing bio-input, comparing bio-input to a standard, indicating a response, etc. Positive and/or dedicated user action in support of such functions is permitted, but no or substantially no such action may be required.

Transparent control as enabled by the present invention may be useful, at least insofar as such transparency avoids the need for a user to dedicate time and/or effort to issuing at least certain commands. For example, when user recognition takes place transparently it may not be necessary for a user to log in, validate his or her identity for security purposes, etc.; nevertheless, account personalization, security, etc. may still be carried out, the difference being that the user may not be compelled to devote time and/or attention to such matters.

Although the example above refers to a head mounted display and a pulse as bio-input, the present invention is not limited only thereto, and other arrangements may be equally suitable.

As already stated, the present invention is not particularly limited with regard to the number, type, position, arrangement, etc. of sensors, nor to the parameters or information that those sensors may detect and/or measure. While the variety of sensors that may be used with the present invention is extremely large, several additional examples are shown herein in FIG. 2 through FIG. 8.

Figure 2:
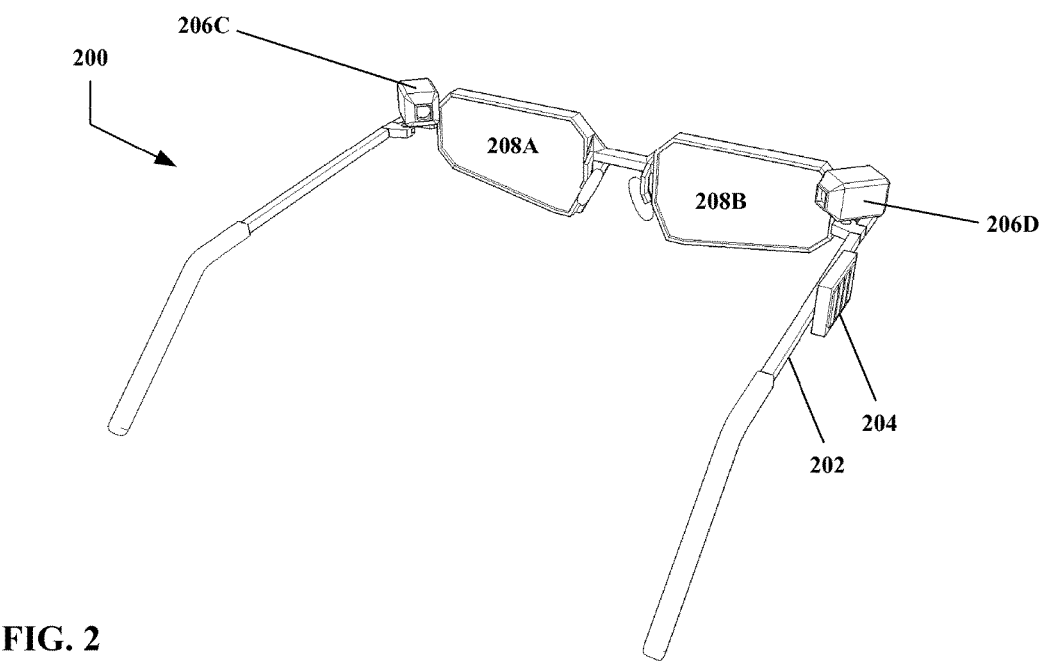
FIG. 2 is a perspective illustration of an example embodiment of an apparatus for user-transparent system control using bio-input according to the present invention, in the form of a head mounted display, with inward-facing image sensors.

FIG. 2 shows an example apparatus 200 for user-transparent system control using bio-input according to the present invention. The apparatus 200 includes a processor 204 disposed on a vehicle 202, the vehicle 202 being in the form of a head mounted display that is similar to a pair of glasses. The apparatus also includes two sensors 206C and 206D. In the example arrangement shown in FIG. 2, the sensors 206C and 206D are imagers, aimed inwardly so as to image (or at least have the ability to image) a user wearing the vehicle 202.

Such an arrangement of sensors 206C, 206D could sense bio-input of a person wearing the vehicle 202 through visual sensing. This might include, but is not limited to, pulse rate, respiration, body temperature, facial color and/or shape (e.g. for face recognition), pupil dilation, iris and/or retinal structure, etc. Furthermore, imagers positioned in certain arrangements may gather additional data, for example imagers in a stereo configuration may generate distance and/or 3D model information, etc.

It is noted that imaging sensors may vary both in design and in function, e.g. sensing visible light in monochrome or color, sensing infrared or ultraviolet light in monochrome or color, sensing thermal radiation, sensing depth/distance through time-of-flight or structured light, etc. The present invention is not particularly limited with regard to either what imaging sensors may be utilized (if imaging sensors are used at all) or what information such imaging sensors may collect.

Figure 3:
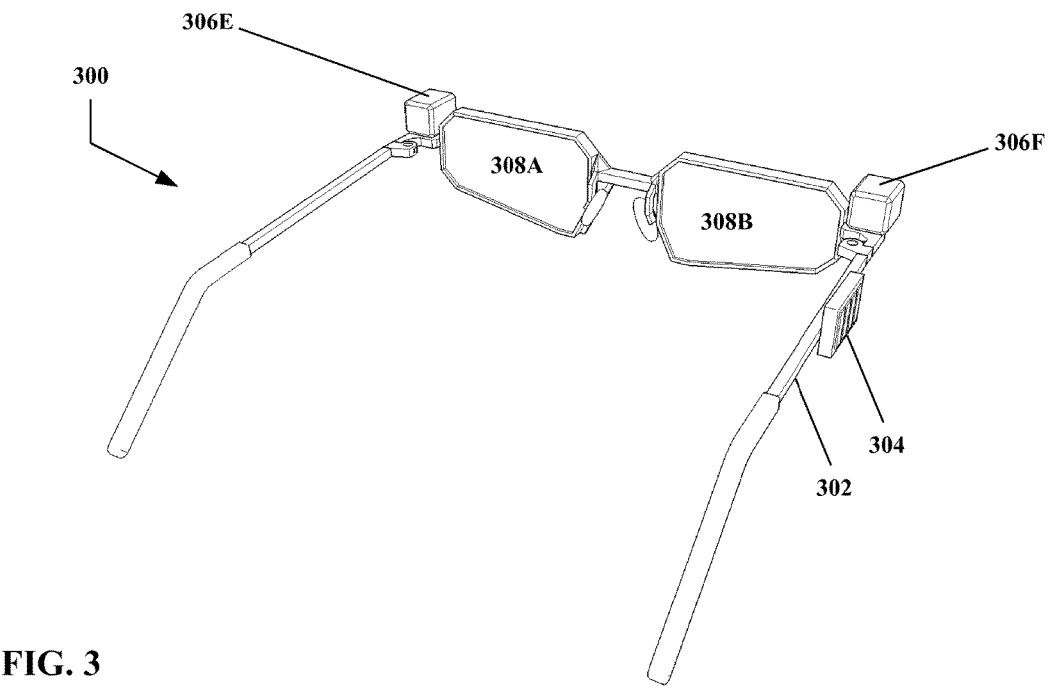
FIG. 3 is a perspective illustration of an example embodiment of an apparatus for user-transparent system control using bio-input according to the present invention, in the form of a head mounted display, with outward facing image sensors.

Turning now to FIG. 3, therein is shown an example apparatus 300 for user-transparent system control using bio-input according to the present invention. The apparatus 300 includes a processor 304 disposed on a vehicle 302, the vehicle 302 being in the form of a head mounted display that is similar to a pair of glasses. The apparatus also includes two sensors 306E and 306F. In the example arrangement shown in FIG. 4, the sensors 306E and 306F are imagers, aimed outwardly so as to image (or at least have the ability to image) in a direction or directions substantially away from the face of a user wearing the vehicle 202.

Although such an arrangement of sensors 306E, 306F may not have a user's face therein, nevertheless such sensors 306E, 306F might sense bio-input of a person wearing the vehicle 302 through sensing body parts thereof that enter the field of view of the sensors 306E, 306F. For example, a user's hands may at least at intervals be visible within the field of view of the sensors 306E, 306F, and bio-input unique to the user and/or otherwise useful may be determined therefrom.

Figure 4:
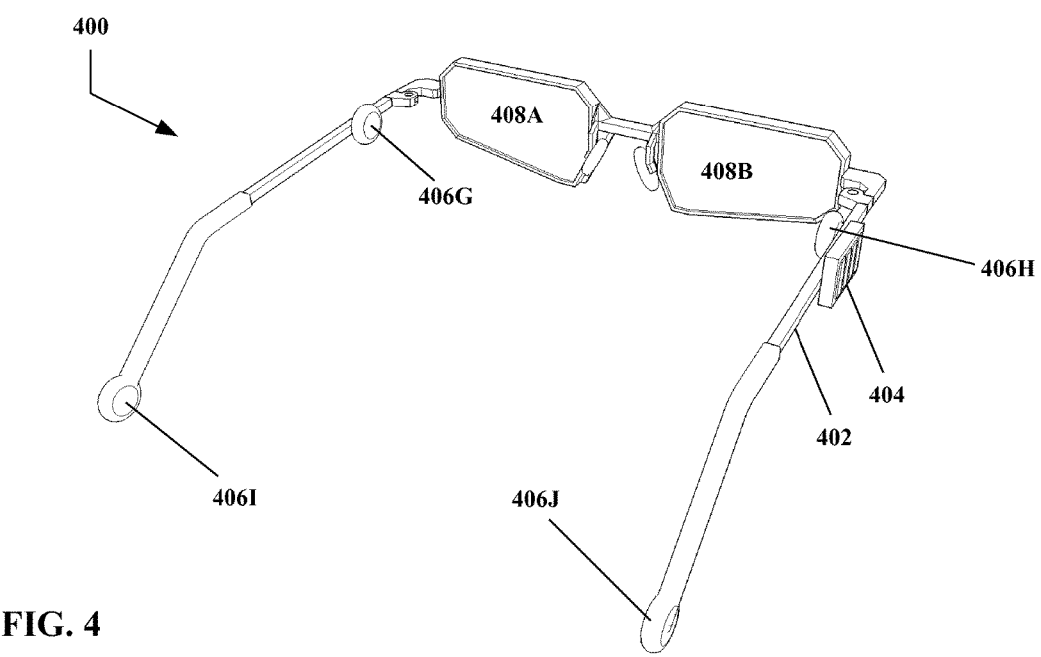
FIG. 4 is a perspective illustration of an example embodiment of an apparatus for user-transparent system control using bio-input according to the present invention, in the form of a head mounted display, with sensor pads proximate the temples and behind the ears.

Moving on to FIG. 4, therein is shown an example apparatus 400 for user-transparent system control using bio-input according to the present invention. The apparatus 400 includes a processor 404 disposed on a vehicle 402, the vehicle 402 being in the form of a head mounted display that is similar to a pair of glasses. The apparatus also includes four sensors 406G, 406H, 406I, and 406J. Sensors 406G and 406H are disposed on the vehicle 402 such that when the vehicle 402 is worn by a user those sensors 406G and 406H are disposed proximate the temples of the user, potentially (though not necessarily) being in contact with the user. Sensors 406I and 406J are disposed on the vehicle 402 such that when the vehicle 402 is worn by a user those sensors 406I and 406J are disposed behind the ears of the user, again potentially (though not necessarily) being in contact with the user.

In the example arrangement shown in FIG. 4, the sensors 406G, 406H, 406I, and 406J are sensor pads, for example as might be adapted to measure electrical conductivity, electric or magnetic signals on the user's skin or within the user's body, tiny motions reflecting blood flow under the skin (i.e. pulse), etc. Such sensors may sense bio-input of a person wearing the vehicle 402 in the form of an electrocardiogram, an electroencephalogram, a magnetocardiogram, a magnetoencephalogram, pulse through physical motion, etc. The precise arrangement of sensors 406G, 406H, 406I, and 406J may vary depending on the specifics of the sensors 406G, 406H, 406I, and 406J themselves, what phenomena the sensors 406G, 406H, 406I, and 406J sense, how that phenomenon is to be sensed, etc.; the present invention is not limited only to the number or configuration of sensors shown.

Furthermore, although the sensors 406G, 406H, 406I, and 406J as shown may be configured so as to serve as contact sensors, other sensors including but not limited to non-contact sensors also may be equally suitable.

Figure 5:
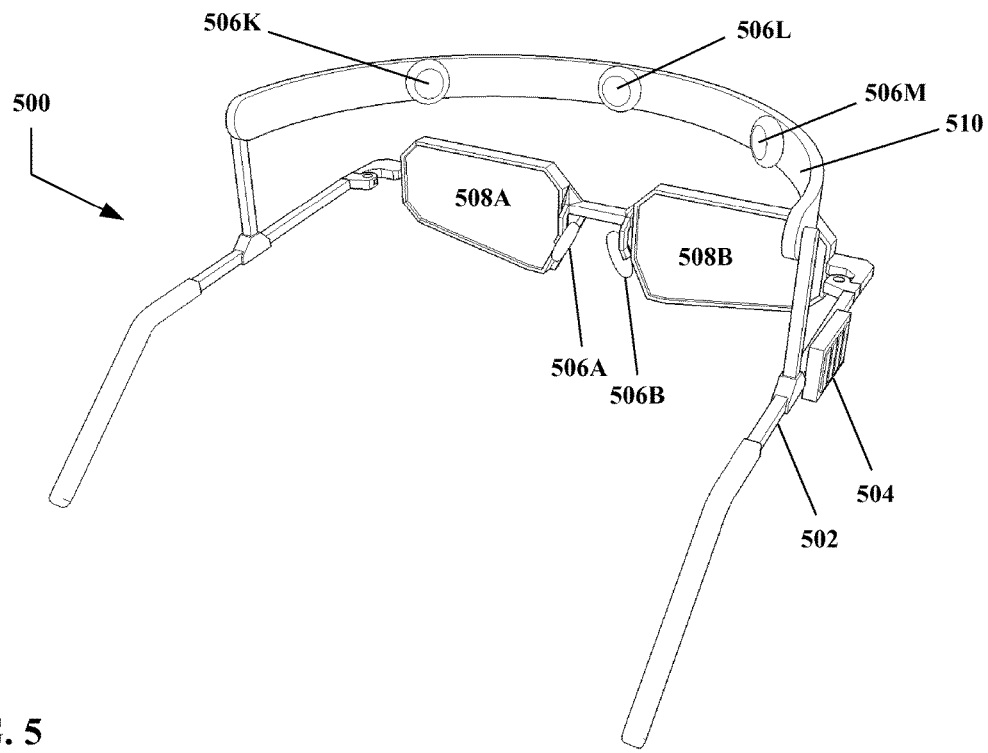
FIG. 5 is a perspective illustration of an example embodiment of an apparatus for user-transparent system control using bio-input according to the present invention, in the form of a head mounted display, with sensor pads proximate the forehead.

Now with reference to FIG. 5, as stated above the present invention is not limited to any particular configuration of sensor pads or other sensors. FIG. 5 shows an example apparatus 500 for user-transparent system control using bio-input according to the present invention. The apparatus 500 includes a processor 504 disposed on a vehicle 502, the vehicle 502 being in the form of a head mounted display that is similar to a pair of glasses. The apparatus also includes three sensors 506K, 506L, and 506M. The sensors 506K, 506L, and 506M are disposed on a support 510 therefor, such that when the vehicle 502 is worn by a user those sensors 506K, 506L, and 506M are disposed proximate the forehead of the user, potentially (though not necessarily) being in contact with the user.

In the example arrangement shown in FIG. 5, the sensors 506K, 506L, and 506M are again sensor pads, for example as might be adapted to measure electrical conductivity, electric or magnetic signals, tiny motions reflecting blood flow under the skin (i.e. pulse), etc. It is emphasized that the present invention is not particularly limited with regard to the number and configuration of sensors 506K, 506L, and 506M.

Figure 6:
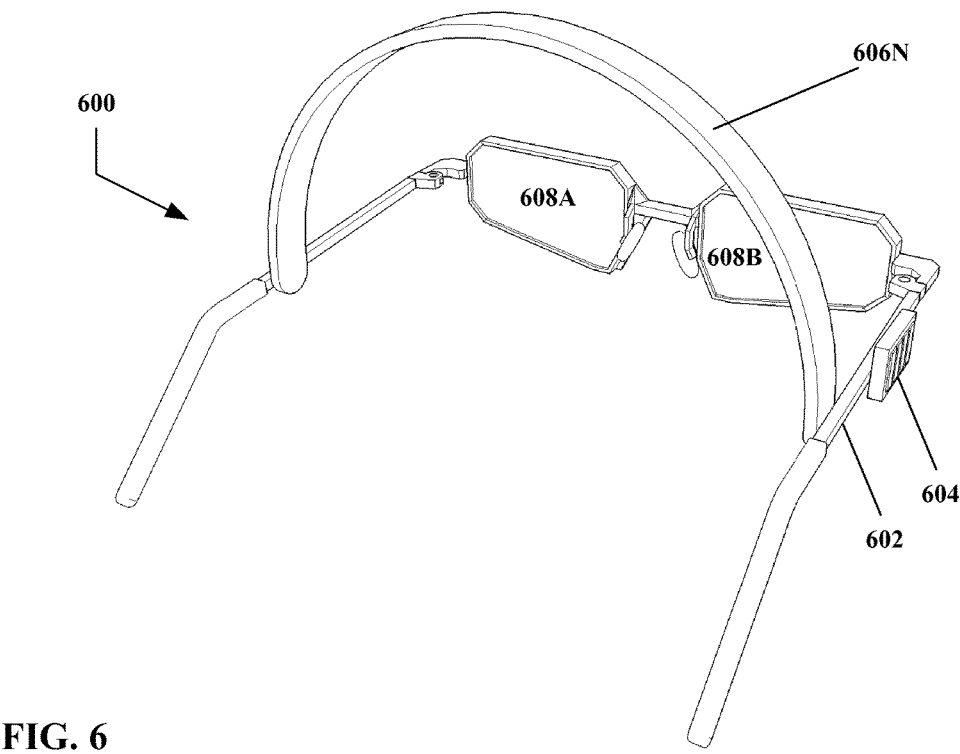
FIG. 6 is a perspective illustration of an example embodiment of an apparatus for user-transparent system control using bio-input according to the present invention, in the form of a head mounted display, with a sensor band extending over the top of the head.

Turning to FIG. 6, therein is shown an example apparatus 600 for user-transparent system control using bio-input according to the present invention. The apparatus 600 includes a processor 604 disposed on a vehicle 602, the vehicle 602 being in the form of a head mounted display that is similar to a pair of glasses. The apparatus also includes a sensor 606N disposed on the vehicle 602 such that when the vehicle 602 is worn by a user the sensor 606N is disposed around and/or above some portion of the user's head, whether in contact with the user or not.

In the example arrangement shown in FIG. 6, the sensor 606N is a continuous band, for example as might be adapted to measure electric or magnetic fields, etc. Such a sensor may be adapted to sense bio-input of a person wearing the vehicle 402 in the form of an electroencephalogram, a magnetoencephalogram, etc. ("brain waves"). Alternately, sensors might generate and/or otherwise actively use electric and/or magnetic fields, for example as in magnetic resonance imaging, so as to reveal internal structure and/or brain activity of the user (whether unique to the user and/or otherwise useful). Other sensors, and/or other arrangements thereof, including but not limited to non-contact sensors, may be equally suitable.

Figure 7:
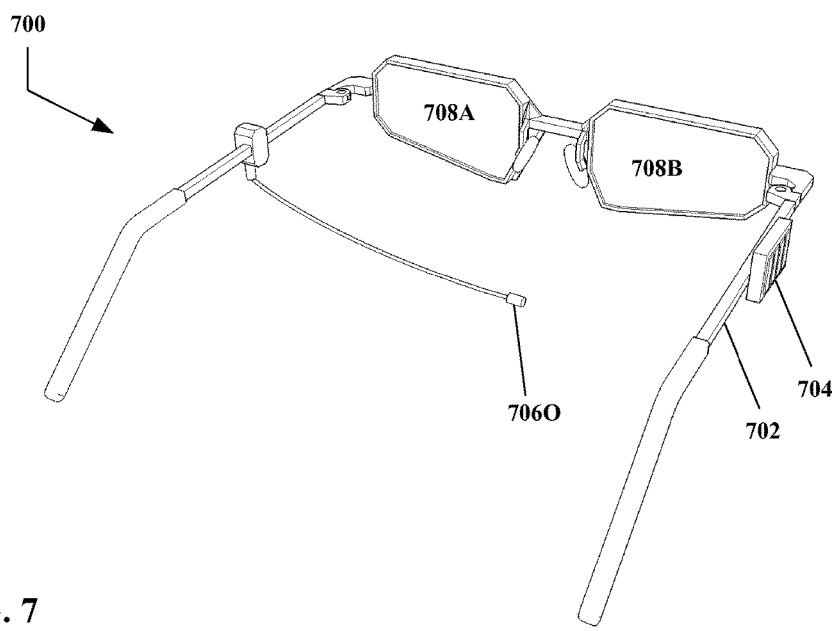
FIG. 7 is a perspective illustration of an example embodiment of an apparatus for user-transparent system control using bio-input according to the present invention, in the form of a head mounted display, with a microphone.

Now with reference to FIG. 7, therein is shown an example apparatus 700 for user-transparent system control using bio-input according to the present invention. The apparatus 700 includes a processor 704 disposed on a vehicle 702, the vehicle 702 being in the form of a head mounted display that is similar to a pair of glasses. The apparatus also includes a sensor 706O in the form of a microphone disposed on the vehicle 702 such that when the vehicle 702 is worn by a user the sensor 706N is disposed proximate the user's mouth.

Such a sensor 706O arrangement could sense bio-input of a person wearing the vehicle 702 through audio sensing. This might include, but is not limited to, speech and/or other vocal patterns, respiration rate, characteristic respiration noise, etc.

Figure 8:
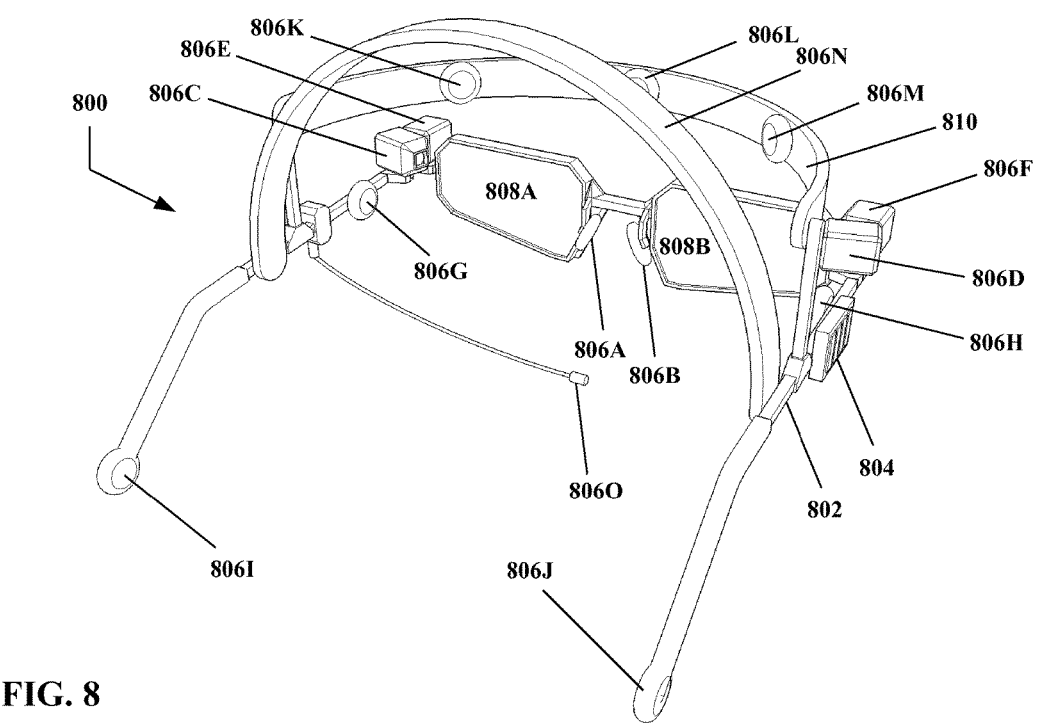
FIG. 8 is a perspective illustration of an example embodiment of an apparatus for user-transparent system control using bio-input according to the present invention, in the form of a head mounted display, with various sensors at multiple locations.

The present invention may incorporate multiple sensors, and/or may use multiple sensors for collecting bio-input from a user. Referring now to FIG. 8, therein is shown an example apparatus 800 for user-transparent system control using bio-input according to the present invention. The apparatus 800 includes a processor 804 disposed on a vehicle 802, the vehicle 802 being in the form of a head mounted display that is similar to a pair of glasses. The apparatus also includes numerous sensors 806A through 806O.

Sensors 806A, 806B, 806G, 806H, 806I, and 806J are shown in the form of sensor pads disposed variously so as to be proximate the bridge of a user's nose, a user's temples, and behind a user's ears. Sensors 806K, 806L, and 806M are shown in the form of sensor pads disposed on a support 810 therefor, so as to be proximate a user's forehead. Sensors 806C, 806D, 806E, and 806F are shown in the form of imagers, variously facing toward or away from a user's face. Sensor 806O is shown in the form of a microphone disposed so as to be proximate a user's mouth.

As may be seen for example from FIG. 8, the present invention is not particularly limited with regard to the number, type, and/or configuration of sensors 806A through 806O thereon. Moreover, although sensors 806A through 806O disposed on the vehicle 802 may be utilized for sensing bio-input, not all sensors 806A through 806O on the vehicle 802 or otherwise incorporated in the apparatus 800 will necessarily sense bio-input, nor are all sensors 806A through 806O required to sense bio-input. For example, forward-facing imagers 806E and 806F might be adapted for imaging an environment (e.g. as part of an augmented reality system) without necessarily also sensing bio-input (though sensing bio-input is not excluded), microphone 806O might be adapted to sense instructions (e.g. voice commands) without necessarily also sensing bio-input, etc.

Figure 9:
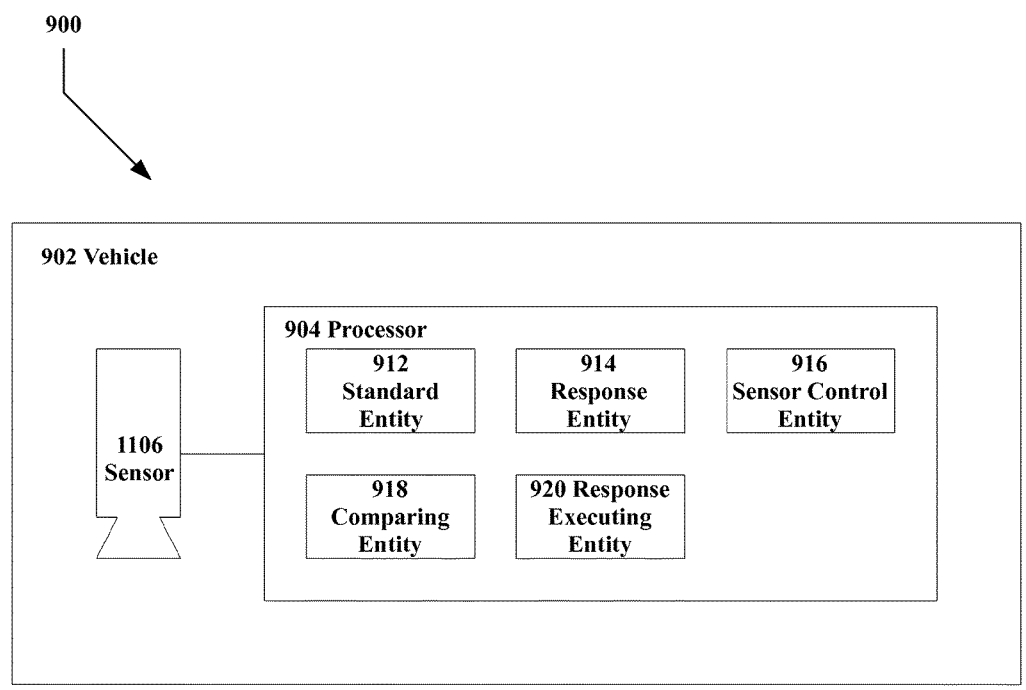
FIG. 9 is a schematic illustration of an example embodiment of an apparatus for user-transparent system control using bio-input according to the present invention, showing data entities instantiated thereon.

Now with reference to FIG. 9, therein a schematic illustration of an apparatus 900 according to the present invention is shown. The apparatus includes a vehicle 902, with a processor 904 and sensor 906 disposed thereon.

In addition, the processor in FIG. 9 includes several data entities 912 through 920 instantiated thereon. As has been noted, the present invention may be executed utilizing executable instructions and/or data instantiated on a processor.

Data entities according to the present invention, including but not limited to the standard entity, are data constructs. That is, data entities are in their essence data, whether records, executable instructions, or other information. Typically though not necessarily, a data entity according to the present invention includes data that is storable on an electronic processor, and/or instructions executable by an electronic processor, however these are examples only and the present invention is not limited only thereto.

In addition, although the various data entities 912 through 920 are shown as distinct entities disposed on the processor 904, this is done for clarity of function only. In at least some embodiments, one or more of the data entities 912 through 920 may be combined together, and/or may be subdivided into components. Likewise, other data entities than those shown in FIG. 9 may be present on the processor 904, whether as part of the present invention or otherwise. Furthermore, the data entities 912 through 920 are not necessarily required to reside at all times on a processor 904, nor necessarily to be ever instantiated onto the processor 904 per se. For example, for some embodiments some or all of the data entities 912 through 920 might be disposed on a data store such as a hard drive, solid state drive, etc., with only those portions immediately utilized as part of the present invention being utilized by the processor 904 at any given time.

The data entities shown disposed on the processor 904 are a standard entity 912, a response entity 914, a sensor control entity 916, a comparing entity 918, and a response executing entity 920.

The standard entity 912 is a data entity adapted to establish a standard for a bio-input according to the present invention. That is, the standard entity establishes what bio-input is to be considered, searched for, etc. Standards and bio-inputs have already been described herein.

For example, a standard entity according to the present invention might include data describing a standard for some form of bio-input. As a more concrete example, a standard entity adapted to establish a standard for bio-input associated with a heartbeat might include data frequency and/or amplitude of electrical signals generated by the heart, algorithms or functions describing waveforms for such electrical signals, plots or models of such waveforms, etc. These are examples only, and the present invention is not limited only thereto.

The response entity 914 is a data entity adapted to establish a response to the sensing of bio-input meeting the standard therefor according to the present invention. That is, the response entity establishes what response is to be executed, how, using what means, etc. Standards and bio-inputs have already been described herein.

The sensor control entity 916 is a data entity adapted to sense bio-input according to the present invention, e.g. using a sensor. That is, the sensor entity actuates, controls, and/or obtains data for comparison against the standard. Sensors and sensing bio-input have already been described herein.

It is noted that for at least certain embodiments, data may come from sensors, e.g. via wired or wireless communication, that are not necessarily under active control of the processor 904. Thus, in certain instances the sensor control entity 916 may or may not literally be in control of a sensor. Rather, for at least certain embodiments the sensor control entity 916 might simply be a passive recipient of data incoming from some source, with (for example) no ability to control or command a sensor. Regardless, so long as bio-input is adapted to be received, the entity adapted to receive that input is nevertheless referred to herein as a sensor control entity 916.

The comparing entity 918 is a data entity adapted to compare bio-input against the standard established therefor according to the present invention. That is, the comparing entity determines whether the bio-input (e.g. as obtained from a sensor) meets the established standard, or not. The comparing entity my incorporate or utilize analysis tools such as mathematical algorithms, graphical comparisons, etc. for determining whether bio-input meets a standard. The present invention is not particularly limited with regard to how the comparison may be carried out.

The response executing entity 920 is a data entity adapted to execute a response if the bio-input meets the standard therefor according to the present invention. That is, the response executing entity 920 carries out whatever result is found by the comparing entity 918: if the comparison is positive (the bio-input meets the standard) the response is executed by the response executing entity 920, while if the comparison is negative (the bio-input does not meet the standard) the response is not executed.

It is emphasized that although certain embodiments of the present invention may utilize data entities such as those shown in FIG. 9, this is an example only, and other arrangements may be equally suitable.

Figure 10:
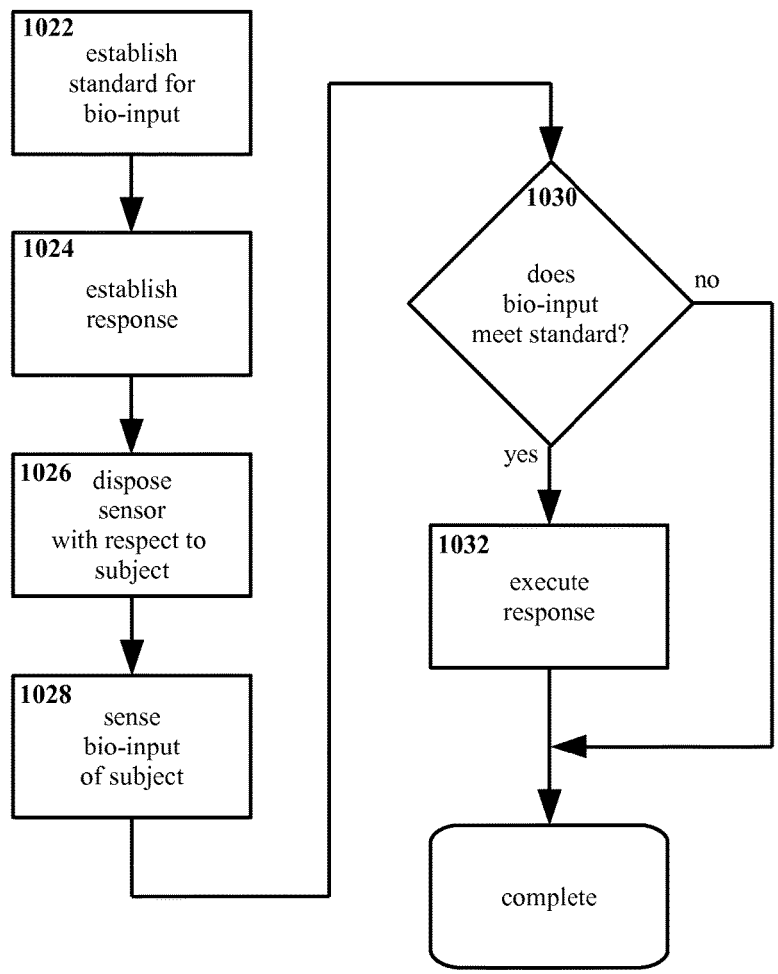
FIG. 10 is a flow chart of an example method for user-transparent system control using bio-input according to the present invention.

Turning now to FIG. 10, an example method for user-transparent system control using bio-input according to the present invention is shown therein.

In the example method of FIG. 10, a standard for bio-input is established 1022. A standard is a condition or set of conditions that may be exhibited by one or more forms of bio-input. For a standard to be satisfied, the conditions therefor must be met. For example, a standard might include data and/or descriptions regarding an electrical signal associated with a human heartbeat; if a heartbeat is sensed that exhibits the specified conditions the standard would be met, while the standard would not be met if no heartbeat were sensed or a heartbeat were sensed that did not exhibit the specified conditions.

Use of heartbeat as a standard is an example only. Standards may include but are not limited to data and/or descriptions regarding magnetic activity associated with a human brain, patterns on a human retina or iris, acoustics of human vocalization and/or respiration, etc. The range of phenomena that may be considered as part of a standard according to the present invention is extremely wide, and the present invention is not particularly limited with respect thereto.

A standard is not necessarily limited only to a single type of bio-input (although standards relating to a single type of bio-input are not excluded). For example, a standard might specify both a parameters associated with a heartbeat and parameters associated with an iris pattern. Thus, in order for the standard to be satisfied, both the heartbeat and the iris of some subject might be required to match those parameters.

Standards may be negative. That is, a standard may specify that some input is not present, or that input that is present does not exhibit some parameter.

In addition, a standard may be sufficiently broad that bio-input from any or substantially any subject may meet such a standard. In such instance, the simple presence of bio-input would be sufficient to meet the standard. For example, a standard might be set for bio-input in the form of a pulse such that any or substantially any heartbeat will satisfy the standard. It will be understood that given such an arrangement, subjects me be determined to be present without necessarily being identified. To continue the above example regarding pulse, a method according to the present invention might consider the mere presence of a pulse as sufficient to execute some response, for example activating an electronic device if that device is worn, touched, held, etc., regardless of who wears, touches, holds, etc. the device.

Standards are not necessarily required to be static. That is, a standard might be variable over time and/or in response to other factors. For example, in the case of a description of a human vocalization being used as a standard, the time of day, temperature, air pressure, humidity, etc. may be considered in determining the specifics of the standard. As a more concrete example, a standard might be configured such that different specific sound pitches, harmonics, etc. may satisfy the standard depending on the ambient air pressure (e.g. under the expectation that voice patterns may to at least some degree depend on the properties of the air carrying those voice patterns).

A standard may be simple or complex. To continue the example above, a simple standard for an electrical signal associated with a human heartbeat might be a number of cycles per minute, i.e. the heart rate, or even the presence of such a signal at all. That is, such a standard might in essence be "a heartbeat is present". A more complex standard for such input might include descriptions of waveform, harmonics, rates of rise and fall, maximum and minimum voltage, etc. The present invention is not particularly limited with regard to complexity of standards.

A standard may be configured so as to enable only a unique individual to meet the standard (although this is not required). That is, an iris standard, pulse standard, retina standard, etc. may be sufficiently specific as to be unique to one individual. Thus, the standard may be a biometric standard. Similarly, a standard may be configured so as to enable only a group of similar individuals, or two or more unique individuals, to meet the standard. However, such arrangements are examples only, and the standard is not required to be a biometric standard, or to uniquely identify an individual or group.

The term "establishing" with regard to bio-input (and likewise response and certain other features of the present invention herein) should be considered broadly. In establishing a standard for bio-input for example, the standard may be loaded into a processor from stored executable instructions, may be defined as a rule set, may be calculated based on data and/or instructions, etc. It is noted that such options—loading, defining, calculating, etc.—are not necessarily exclusive, and a single embodiment may utilize more than one. The manner by which the standard for bio-input is established is not particularly limited.

Continuing in FIG. 10, a response is established 1024. A response is some action that may be taken if the standard (established in step 1022) is satisfied. The present invention is not particularly limited with regard to what actions responses may include. Responses typically are, but are not required to be, instructions to and/or actions taken by a processor or a device with a processor therein. Suitable responses may include, but are not limited to, turning on a system such as an electronic device or processor, setting preferences for a system, executing instructions on a system, delivering messages to or through a system, and other responses associated with operating and/or controlling such a system. Suitable responses also may include communicating information, for example the bio-input, the time at which the bio-input was sensed, the location at which the bio-input was sensed, the identity of the subject from whom the bio-input was sensed (for example if the subject is identified from that bio-input), the identity of a processor and/or apparatus (e.g. using a serial number or other identifier stored within the processor), etc.

A sensor is disposed with respect to a subject 1026. That is, a sensor is placed in a position and/or state so as to be adapted to sense a subject. Disposing the sensor may include directly positioning a sensor on and/or near a subject, e.g. securing the sensor to a subject (for contact sensors such as skin electrodes) or aiming the sensor at a subject (for non-contact sensors such as imagers).

However, disposing the sensor also may include positioning the sensor on or in some object, environment, etc. without a subject necessarily being present currently, but arranged such that the sensor will be in position to sense a subject at a relevant time. Considering as an example a head mounted display, positioning an imager on the head mounted display such that when a subject wears the head mounted display, the imager is configured so as to image the subject's iris, would constitute disposing the sensor with respect to the subject 1026 according to the present invention. Thus, there is no requirement to position a sensor near a subject at any given time, so long as the sensor may in use be positioned suitably with respect to the subject so as to sense the subject at a relevant time.

The present invention is not particularly limited with regard to how or where sensors may be disposed, what sort of sensors may be utilized, and/or how data may be sensed and/or stored.

Moving on in FIG. 10, the bio-input of a subject is sensed 1028. The details of how bio-input is sensed 1028 will depend at least in part on the standard for bio-input (established in step 1022) and/or the manner by which the sensor is disposed with respect to the subject (in step 1026). However, the present invention is not particularly limited with regard to sensing bio-input.

A determination is made as to whether the bio-input meets the standard therefor 1030. The details of the determination will depend at least in part on the standard for bio-input (established in step 1022). Typically, though not necessarily, the determination will be made using a processor, e.g. a processor executing instructions instantiated thereon, though this is an example only and other arrangements may be equally suitable.

If the determination 1030 is positive—that is, if the bio-input meets the standard established therefor—the method proceeds to step 1032. If the determination 1030 is negative—if the bio-input does not meet the standard established therefor—then step 1032 is skipped.

Continuing in FIG. 10, the response is executed 1032 (the response having been established in step 1024). As noted, if the determination 1030 was negative, the step of executing the response 1032 is skipped.

The particulars regarding the execution of the response 1032 may depend at least in part on the details of step 1024, wherein the response was established. That is, the response executed 1032 will be the response established in step 1024 (or one such response, if multiple responses were established in step 1024).

Although FIG. 10 shows the method therein as being complete following step 1032, it is emphasized that the method in FIG. 10 is an example only. Other steps, other functions, etc. may be incorporated into the method, and/or other methods may be executed in combination with the method according to the present invention. In addition, for at least certain embodiments the method may repeat, e.g. in an ongoing loop including steps 1028 and 1030 so as to continues to sense bio-input 1028 and determine if that bio-input meets the standard therefor 1030 (potentially executing the response 1032 if the bio-input does meet the standard).

Figure 11:
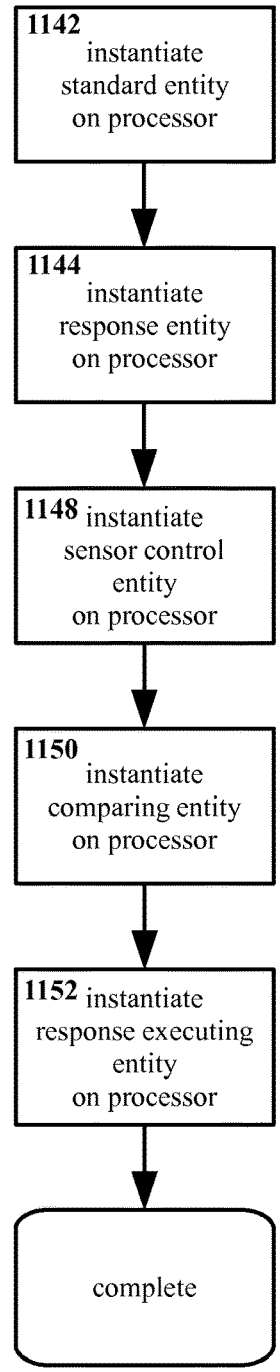
FIG. 11 is a flow chart of another example method for establishing user-transparent system control using bio-input according to the present invention.

Turning now to FIG. 11, as has been noted previously certain embodiments of the present invention may be executed as a machine-implemented method. For example, method steps may be executed on a data processor. In addition, a definitions may be loaded onto and/or defined on a data processor, and/or executable instructions instantiated thereon, so as to enable execution of method steps according to the present invention. FIG. 11 shows such an arrangement.

In the example arrangement of FIG. 11, a standard entity is instantiated on a processor 1142. A standard entity is a data entity adapted to establish a standard for a bio-input according to the present invention. Standard entities have already been described herein.

A response entity is instantiated on a processor 1144. The response entity is a data entity adapted to establish a response to the sensing of bio-input meeting the standard therefor according to the present invention. Response entities have already been described herein.

A sensor control entity is instantiated on a processor 1148. The sensor control entity is a data entity adapted to sense bio-input according to the present invention, e.g. using a sensor. Sensor control entities have already been described herein.

A comparing entity is instantiated on a processor 1150. The comparing entity is a data entity adapted to compare bio-input against the standard established therefor according to the present invention. Comparing entities have already been described herein.

A response executing entity is instantiated on a processor 1152. The response executing entity is a data entity adapted to execute a response if the bio-input meets the standard therefor according to the present invention. Response executing entities have already been described herein.

The above specification, examples, and data provide a complete description of the manufacture and use of the composition of the invention. Since many embodiments of the invention can be made without departing from the spirit and scope of the invention, the invention resides in the claims hereinafter appended.

We claim:

1. An apparatus, comprising:
a vehicle adapted to be worn by an individual without restricting activity of the individual;
a first sensor disposed on the vehicle, the first sensor to sense a cardiac wave of the individual with substantially no dedicated sensing action required from the individual and with sufficient sensitivity to identify the individual using a characteristic heart function of the body of the individual;
a second sensor disposed on the vehicle, the second sensor to measure a variable input with substantially no dedicated sensing action required from the individual;
a processor coupled to the first sensor, wherein the processor is to:

identify a standard cardiac wave associated with the individual;
receive the variable input from the second sensor;
adjust the standard cardiac wave associated with the individual in view of the variable input to obtain an adjusted standard cardiac wave;
compare data representative of the cardiac wave with data representative of the adjusted standard cardiac wave associated with the individual; and
in response to data representative of the cardiac wave matching the data representative of the adjusted standard cardiac wave, perform a first subject service associated with the cardiac wave and the individual without any direct interaction by the individual with the apparatus.

2. The apparatus of claim 1, wherein the vehicle comprises a head-mounted display.

3. The apparatus of claim 1, wherein the first sensor comprises at least one of an electrocardiogram, a magnetocardiogram, a monochromatic visible light imager, a color visible light imager, a monochromatic near-infrared imager, a color near-infrared imager, a spectrometer, or an imaging spectrometer.

4. The apparatus of claim 1, wherein the first sensor is a contact sensor.

5. The apparatus of claim 1, wherein the first sensor is a non-contact sensor.

6. The apparatus of claim 1, wherein the first sensor is disposed on the vehicle such that when the individual wears said the vehicle, the first sensor is proximate a bridge of a nose of the individual.

7. The apparatus of claim 1, wherein the first sensor is disposed on the vehicle such that when the individual wears the vehicle, the first sensor is proximate a temple of the individual.

8. The apparatus of claim 1, wherein the first sensor is disposed on the vehicle such that when the individual wears the vehicle, the first sensor is behind and proximate an ear of the individual.

9. The apparatus of claim 1, wherein the first sensor is disposed on the vehicle such that when the individual wears the vehicle, the first sensor is proximate a forehead of the individual.

10. The apparatus of claim 1, wherein the first sensor is removably engaged with the vehicle.

11. The apparatus of claim 1, wherein the first subject service comprises at least one of activating an entity, authorizing access to the entity, or activating a preference of the entity.

12. The apparatus of claim 11, wherein the entity comprises at least one of an electronic device, an electronic device component, or a data entity storing executable instructions.

13. The apparatus of claim 1, wherein the apparatus further comprises a communicator adapted to communicate between the processor and an external entity.

14. The apparatus of claim 13, wherein the first subject service comprises establishing communication between the processor and the external entity.

15. The apparatus of claim 14, wherein the first subject service comprises communicating at least one of the data representative of the cardiac wave, data representative of a time of sensing said cardiac wave, or data representative of a location of sensing the cardiac wave to the external entity.

16. The apparatus of claim 1, wherein the processor is operable to record data.

17. The apparatus of claim 16, wherein the processor is operable to record at least one of the data representative of the cardiac wave, data representative of a time of sensing said cardiac wave, or data representative of a location of sensing the cardiac wave.

18. The apparatus of claim 1, wherein:
the first sensor is operable to repeatedly sense the cardiac wave;
the processor is operable to repeatedly compare the data representative of the cardiac wave with the data representative of the adjusted standard cardiac wave; and
the processor is operable to repeatedly perform the first subject service.

19. The apparatus of claim 1, wherein:
the first sensor is operable to substantially continuously sense the cardiac wave;
the processor is operable to substantially continuously compare the data representative of the cardiac wave with the data representative of the adjusted standard cardiac wave; and
the processor is operable to substantially continuously perform the first subject service.

20. The apparatus of claim 1, wherein the cardiac wave is dynamic.

21. The apparatus of claim 1, wherein the first sensor is shaped to engage the body of the individual at a first location and a second location, wherein the processor is to:
perform the subject service associated with the cardiac wave and the individual when the first sensor is engaged at first location and the data representative of the cardiac wave matches the data representative of the adjusted standard cardiac wave; and
update the adjusted standard cardiac wave and perform the subject service when the first sensor located at the second location and the data representative of the cardiac wave matches data representative of the updated adjusted standard cardiac wave.

22. A method, comprising:
transparently sensing, by a first sensor, a cardiac wave from an individual at a first location on a body of the individual without restricting activity of the individual, wherein:
the first location is a place on the body for measuring the cardiac wave for a cardiac system of the body;
the first sensor being adapted to sense the cardiac wave with substantially no dedicated sensing action required from the individual and with sufficient sensitivity as to identify the individual using a characteristic heart function of the body;
identifying, by a processor, a standard cardiac wave associated with the individual;
receiving the variable input from a second sensor;
adjusting the standard cardiac wave associated with the individual in view of the variable input to obtain an adjusted standard cardiac wave;
comparing data representative of the cardiac wave with data representative of the adjusted standard cardiac wave associated with the individual; and
in response to data representative of the cardiac wave matching the data representative of the adjusted standard cardiac wave, transparently performing a first subject service associated with the cardiac wave and the individual without any direct interaction by the individual with the apparatus.

23. The method of claim 22, further comprising sensing the cardiac wave using at least one of electrocardiography, magnetocardiography, monochromatic visible light imaging, color visible light imaging, monochromatic near-infrared imaging, color near-infrared imaging, spectrometry, or imaging spectrometry.

24. The method of claim 22, further comprising sensing the cardiac wave via contact sensing.

25. The method of claim 22, further comprising sensing the cardiac wave via non-contact sensing.

26. The method of claim 22, wherein the first sensor is located proximate a bridge of a nose of the individual.

27. The method of claim 22, wherein the first sensor is located behind and proximate an ear of the individual.

28. The method of claim 22, wherein the first sensor is located proximate a forehead of the individual.

29. The method of claim 22, wherein the first sensor is disposed on the vehicle and is adapted to be worn by the individual.

30. The method of claim 22, wherein transparently performing the first subject service further comprises at least one of activating an entity, authorizing access to the entity, or activating a preference of the entity.

31. The method of claim 30, wherein the entity comprises at least one of an electronic device, an electronic device component, or a data entity operable to store executable instructions.

32. The method of claim 22, wherein performing the first subject service further comprises performing the first subject service in an augmented reality environment or a virtual reality environment.

33. The method of claim 22, wherein performing the first subject service further comprises establishing a communication channel between the processor and an external entity.

34. The method of claim 22, wherein performing the first subject service further comprises communicating at least one of the data representative of the cardiac wave, data representative of a time of sensing the cardiac wave, or data representative of a location of sensing the cardiac wave to the external entity.

35. The method of claim 22, further comprising recording at least one of the data representative of the cardiac wave, data representative of a time of sensing the cardiac wave, or data representative of a location of sensing the cardiac wave.

36. The method of claim 22, comprising:
repeatedly sensing the cardiac wave with the first sensor;
repeatedly comparing the data representative of the cardiac wave with the data representative of the adjusted standard cardiac wave; and
in response to the data representative of the cardiac wave repeatedly matching the data representative of the adjusted standard cardiac wave, repeatedly and transparently performing the first subject service.

37. The method of claim 22, comprising:
substantially and continuously sensing with the cardiac wave with the first sensor;
substantially continuously comparing the data representative of the cardiac wave with the data representative of the adjusted standard cardiac wave; and
in response to the data representative of the cardiac wave repeatedly matching the data representative of the adjusted standard cardiac wave, substantially and continuously performing the first subject service.

38. The method of claim 22, wherein the cardiac wave is dynamic.

39. The method of claim 22, wherein the first sensor is shaped to engage the body of the individual at the first location and a second location, wherein the method further comprises:

performing the subject service associated with the cardiac wave and the individual when the first sensor is engaged at the first location and the data representative of the cardiac wave matches the data representative of the adjusted standard cardiac wave; and
updating the adjusted standard cardiac wave and performing the subject service when the first sensor located at the second location and the data representative of the cardiac wave matches data representative of the updated adjusted standard cardiac wave.

40. An apparatus, comprising:
a vehicle shaped to be worn transparently by an individual without restricting activity of the individual, the vehicle comprising a head-mounted display;
a first sensor disposed on the vehicle such that when the individual wears the vehicle, the first sensor is proximate a bridge of a nose of the individual, wherein the first sensor comprises a color visible light imaging sensor operable to sense a cardiac wave of the individual with sufficient sensitivity to enable identification of the individual by a characteristic heart function of a body of the individual; and
a processor coupled to the first sensor, wherein the processor is to:
identify a standard cardiac wave associated with the individual;
receive a variable input from a second sensor;
adjust the standard cardiac wave associated with the individual in view of the variable input to obtain an adjusted standard cardiac wave;
repeatedly compare data representative of the cardiac wave with data representative of the adjusted standard cardiac wave associated with the individual;
in response to data representative of the cardiac wave matching the data representative of the adjusted standard cardiac wave, transparently performing a first subject service, the first subject service comprising at least one of activating an entity, authorizing access to the entity, or activating a preference of the entity, the entity comprising at least one of an electronic device, an electronic device component, or a data entity operable to store executable instructions; and
record at least one of the data representative of the cardiac wave, data representative of a time of sensing said cardiac wave, or data representative of a location of sensing the cardiac wave.

41. The apparatus of claim 40, wherein the first sensor is shaped to engage the body of the individual at a first location and a second location, wherein the processor is to:
perform the subject service associated with the cardiac wave and the individual when the first sensor is engaged at first location and the data representative of the cardiac wave matches the data representative of the adjusted standard cardiac wave; and
update the adjusted standard cardiac wave and perform the subject service when the first sensor located at the second location and the data representative of the cardiac wave matches data representative of the updated adjusted standard cardiac wave.

42. A method, comprising:
sensing, by a first sensor, a cardiac wave of an individual, the sensing requiring substantially no dedicated sensing action from the individual;
sensing, by a second sensor, a variable input with substantially no dedicated sensing action required from the individual;

identifying a standard cardiac wave associated with the individual;

receiving the variable input from the second sensor;

adjusting the standard cardiac wave associated with the individual in view of the variable input to obtain an adjusted standard cardiac wave;

comparing the cardiac wave with the adjusted standard cardiac wave; and in response to data representative of the cardiac wave matching the data representative of the adjusted standard cardiac wave, executing a response associated with the cardiac wave and the individual, the response comprising at least one of activating an entity, authorizing access to the entity, or activating preferences in the entity, the entity comprising at least one of an electronic device, an electronic device component, or a data entity operable to store executable instructions.

43. The method of claim 42, wherein the first sensor is shaped to engage the body of the individual at a first location and a second location, wherein the method further comprises:

performing the subject service associated with the cardiac wave and the individual when the first sensor is engaged at first location and the data representative of the cardiac wave matches the data representative of the adjusted standard cardiac wave; and updating the adjusted standard cardiac wave and performing the subject service when the first sensor located at the second location and the data representative of the cardiac wave matches data representative of the updated adjusted standard cardiac wave.

44. An apparatus, comprising:

means for disposing a first sensor on a vehicle adapted to be worn by an individual so as to enable transparently engagement at a first location on a body of the individual without restricting activity of the individual, wherein the first location is a place on the body for measuring a cardiac wave for a cardiac system of the body;

means for disposing a second sensor on the vehicle, the second sensor to measure a variable input with substantially no dedicated sensing action required from the individual;

means for sensing the cardiac wave from the individual, wherein the first sensor is operable to sense the cardiac wave with substantially no dedicated sensing action required from the individual and with sufficient sensitivity to identify the individual using a characteristic heart function of the body;

means for identifying a standard cardiac wave associated with the individual;

means for receiving the variable input from the second sensor;

means for adjusting the standard cardiac wave associated with the individual in view of the variable input to obtain an adjusted standard cardiac wave;

means for comparing data representative of the cardiac wave with data representative of the adjusted standard cardiac wave associated with the individual; and means for, in response to data representative of the cardiac wave matching the data representative of the adjusted standard cardiac wave, transparently perform a subject service, the subject service comprising at least one of a communication function, an augmented reality function, a virtual reality function, a videogame, heads-up information, or a navigation information.

45. The apparatus of claim 44, wherein the first sensor is shaped to engage the body of the individual at the first location and a second location, the apparatus further comprising:

means for performing the subject service associated with the cardiac wave and the individual when the first sensor is engaged at the first location and the data representative of the cardiac wave matches the data representative of the adjusted standard cardiac wave; and means for updating the adjusted standard cardiac wave and perform the subject service when the first sensor located at the second location and the data representative of the cardiac wave matches data representative of the updated adjusted standard cardiac wave.

* * * * *